United States Patent [19]

Bailey et al.

[11] Patent Number: 5,163,926

[45] Date of Patent: Nov. 17, 1992

[54] SUCTION METERING AND MIXING DEVICE

[75] Inventors: James C. Bailey, Yellow Springs; Gordon E. Atkinson, Cedarville, both of Ohio

[73] Assignee: Vernay Laboratories, Inc., Yellow Springs, Ohio

[21] Appl. No.: 665,823

[22] Filed: Mar. 7, 1991

Related U.S. Application Data

[63] Continuation-in-part of Ser. No. 526,086, May 21, 1990.

[51] Int. Cl.[5] .............................................. A61M 5/00
[52] U.S. Cl. ...................................... 604/269; 604/19; 604/35; 604/38; 604/902
[58] Field of Search .................. 604/265, 269, 119, 21, 604/22, 902, 4, 19, 35, 38, 89

[56] References Cited

U.S. PATENT DOCUMENTS

| | | | |
|---|---|---|---|
| 4,002,170 | 1/1977 | Hansen et al. | 604/269 |
| 4,356,823 | 11/1982 | Jackson | 604/35 X |
| 4,447,191 | 5/1984 | Bilstad et al. | 417/12 |
| 4,516,398 | 5/1985 | Wuchinich | 604/22 |
| 4,540,406 | 9/1985 | Miles | 604/269 |
| 4,547,186 | 10/1985 | Bartlett | 604/4 |
| 4,675,117 | 6/1987 | Neumann et al. | 210/189 |
| 4,729,764 | 3/1988 | Gualtier | 604/38 |
| 4,744,785 | 5/1988 | Rosenthal et al. | 604/4 |
| 4,769,001 | 9/1988 | Prince | 604/4 |
| 4,775,360 | 10/1988 | Lane et al. | 604/4 |
| 4,834,890 | 5/1989 | Brown et al. | 210/789 |
| 4,863,590 | 9/1989 | Ohnishi et al. | 210/93 |
| 4,874,364 | 10/1989 | Morris et al. | 604/35 |
| 4,981,466 | 1/1991 | Lumbert | 604/19 |

*Primary Examiner*—Robert A. Hafer
*Assistant Examiner*—Kerry Owens
*Attorney, Agent, or Firm*—Biebel & French

[57] ABSTRACT

A suction metering and mixing device is disclosed for collecting body fluids such as blood and simultaneously mixing an anticoagulant therewith. The device includes a suction passage having an inlet end and an opposite end for connection to a vacuum supply. A chamber is provided for controlling the flow of anticoagulant and includes a movable passage for conveying anticoagulant into the chamber and a diaphragm dividing the chamber into first and second portions wherein the movable passage may be moved from a position spaced from the diaphragm to a use position in contact with the diaphragm to prevent flow of anticoagulant into the first chamber portion. A fluid connection is provided between the suction passage and the second chamber portion whereby a vacuum may be supplied to the second chamber portion from the suciton passage and the diaphragm is drawn away from the movable passage to allow anticoagulant to flow into the first chamber portion. The anticoagulant then flows through a supply tube to a position adjacent to the inlet to the suction passage where it is mixed with blood entering the suction passage.

15 Claims, 6 Drawing Sheets

SUCTION METERING AND MIXING DEVICE

CROSS-REFERENCE TO RELATED APPLICATION

This is a continuation-in-part of application Ser. No. 526,086, filed May 21, 1990.

BACKGROUND OF THE INVENTION

The present invention relates to a suction device for aspirating blood during a surgical procedure and, more particularly, to a device for adding and mixing an anticoagulant with blood as it is sucked into the device.

During surgical procedures, especially those involving the abdominal or chest cavities, a great deal of bleeding occurs normally and conventional practice has been to simply aspirate the blood and other fluids to keep the surgical site clear and subsequently dispose of the fluids so removed.

An increasingly utilized method in this area has been to convey the blood and other fluids which are aspirated during surgery to a centrifuge, extract the red blood cells and serum and return the thus purified fractions to the patient during the surgical procedure. Since the blood begins to clot immediately upon contact with air, it is necessary to add an anticoagulant to the fluids aspirated, preferably as they are removed from the patient.

During this type of procedure, it is common to provide the operator with a on/off switch or clamp to terminate the suction and flow of the anticoagulant when the aspirator is not needed. Besides being somewhat awkward, it is not uncommon for the operator not to turn off the flow of anticoagulant, particularly in an emergency situation. As a result, an excess of anticoagulant may be added to the aspirated blood, thus increasing the rate of bleeding as the blood is returned to the patient.

U.S. Pat. No. 4,547,186 to Bartlett discloses a device for automatically introducing an anticoagulant into aspirated blood. In this device a bag of anticoagulant is provided for supplying anticoagulant at the point of aspiration as well as at a point along the blood flow line between the suction nozzle and the collection bag. However, the anticoagulant bag must be positioned at a particular height relative to the suction nozzle for the system to operate properly. Thus, it can be seen that this system requires a certain amount of calibration prior to use which may prove to be inconvenient in emergency situations.

Another system for metering anticoagulant during aspiration of blood is shown in U.S. Pat. No. 4,540,406 to Miles in which anticoagulant may be accurately metered to a suction nozzle regardless of the height difference between the nozzle and the anticoagulant supply. The suction nozzle of this device requires that the operator place his or her finger over an opening in the nozzle side in order to actuate the suction. While this device provides an improved amount of control over termination of the suction, the operator is required to give additional attention in placing his or her finger over the opening in the suction nozzle and as such introduces an increased amount of inconvenience into the aspiration procedure.

Accordingly, what is needed is a device forr aspirating fluids from a patient during a surgical procedure which is capable of accurately metering anticoagulant for mixing with the aspirated fluids, and which must be capable of initiating and terminating flow of anticoagulant upon initiation and termination of the flow of fluids through the suction device such that a minimum of attention from the operator is required during use of the device.

SUMMARY OF THE INVENTION

The present invention is directed toward a suction metering and mixing device which may be used to remove fluids from the body cavity of a patient during surgical procedures.

The suction metering and mixing device of the present invention includes a suction passage for sucking a first fluid such as blood into the device. Means are also provided for supplying a second fluid such as anticoagulant to the suction passage as the first fluid is sucked into the device.

A chamber is provided for controlling the flow of the second fluid toward the suction passage whereby the flow of the second fluid is initiated in response to the presence of the first fluid within the suction passage, and is terminated in response to the absence of the first fluid within the suction passage. The chamber includes an inlet port defining a passage for entry of the second fluid which is conveyed from a container for supplying the second fluid.

A diaphragm divides the chamber into a first fluid supply portion and a second vacuum portion wherein the inlet port is in fluid communication with the first chamber portion. The diaphragm is normally located in a rest position in contact with the inlet port such that flow of the second fluid into the first chamber portion is prevented.

A fluid connection is provided between the second chamber portion and the suction passage intermediate a first end of the suction passage for receiving the first fluid and a second end of the suction passage which is adapted for connection to a vacuum source. When the first fluid is present within the suction passage, the vacuum source connected to the second end of the suction passage causes air to be drawn from the second chamber portion through the fluid connection such that a vacuum is supplied to the second chamber portion. The resulting sub-atmospheric pressure within the second chamber portion causes the diaphragm to be repositioned away from the inlet port of the first chamber portion to allow the second fluid to flow into the first chamber portion.

The first chamber portion is further provided with an outlet port such that the second fluid flowing into the first chamber portion is drawn through the outlet port and into a tube which carries it to the first end of the suction passage. The second fluid is sucked into the suction passage with the first fluid whereby the first and second fluids are mixed together at the entry point to the suction metering and mixing device.

Thus, the present device provides on-demand metering of the second fluid to be mixed with the first fluid such that the second fluid will only be supplied when the first fluid is present in the suction passage. In addition, when the device is no longer drawing the first fluid into the suction passage, the vacuum in the suction passage will be released as a limited volume flow of air is drawn into the passage and the diaphragm will return to its rest position in contact with the inlet port to terminate the flow of the second fluid.

Further, the present invention provides a device for aspirating fluids from a patient in which a minimum of attention is required for ccontrolling the flow of anticoagulant to be mixed with aspirated fluids.

In an alternative embodiment of the present invention, the fluid regulating portion of the suction metering and mixing device is modified wherein the first chamber portion includes a plunger forming an intermediate passage between the inlet port for the second fluid and the outlet port.

In a storage position of the plunger, a first end of the intermediate passage is positioned in spaced relation to the diaphragm such that the diaphragm rests in an unstressed position. The plunger may be moved forwardly to an operational position wherein the first end of the intermediate passage contacts and flexes the diaphragm and the diaphragm forms a closure over the first end. In addition, a second end of the intermediate passage opens into a slot on the side of the plunger which is in fluid communication with the inlet port.

The fluid regulator of this embodiment works in a manner similar to that of the previous embodiment and provides means whereby the suction metering and mixing device may be stored with the diaphragm in an unstressed condition. In this manner, problems associated with the diaphragm becoming set in a flexed position are avoided, and a predetermined closure force may be established between the first end of the intermediate passage and the diaphragm at the time when the metering and mixing device is put into use. This embodiment also has the advantage that, in the storage position, the second fluid is easily primed from its container through to the device inlet.

Other objects and advantages of the invention will be apparent from the following description, the accompanying drawings and the appended claims.

DETAILED DESCRIPTION OF THE PREFERRED EMBODIMENT

Figure 1:
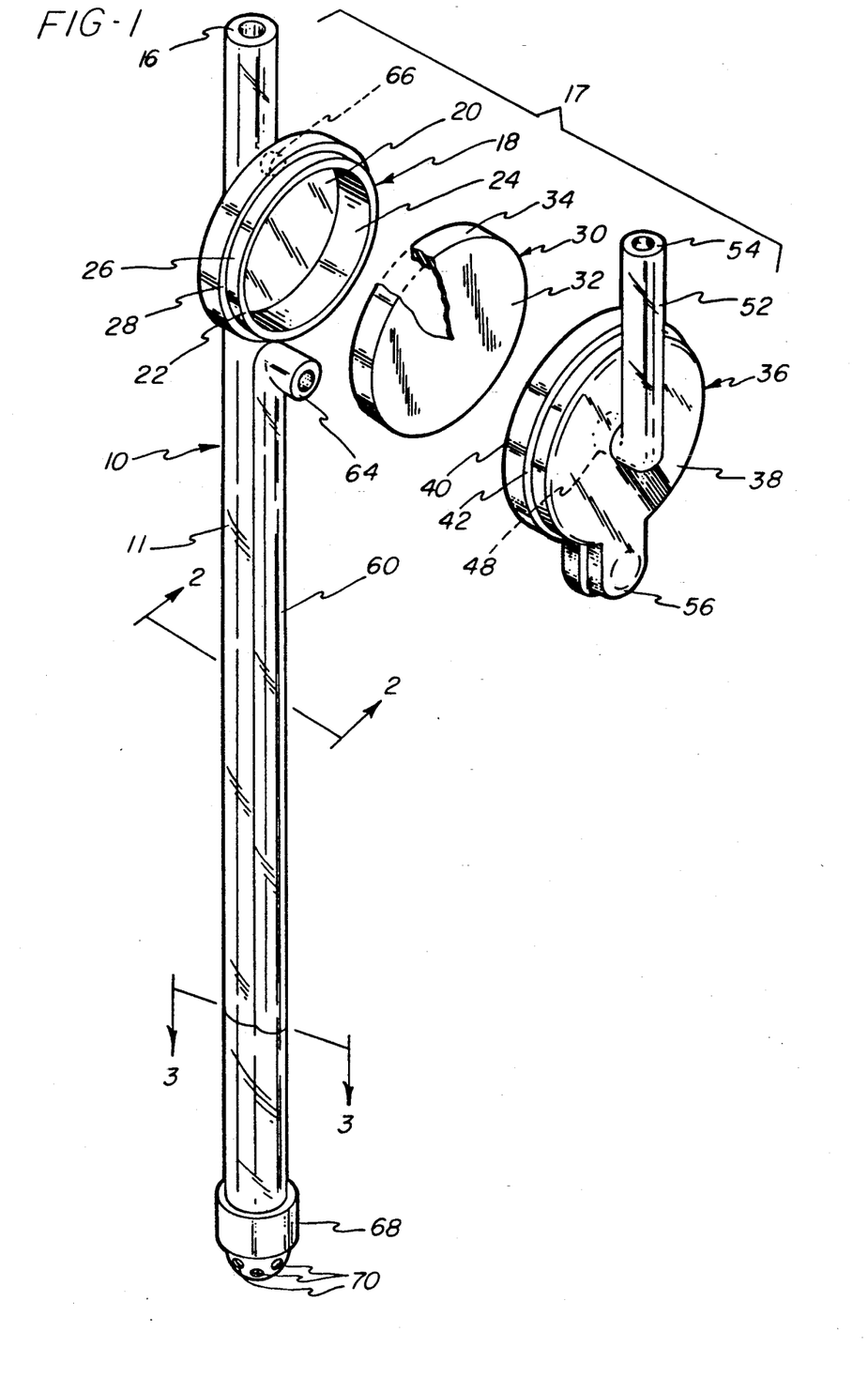
FIG. 1 is an exploded perspective view of the suction metering and mixing device of the present invention.
Figures 2, 3:
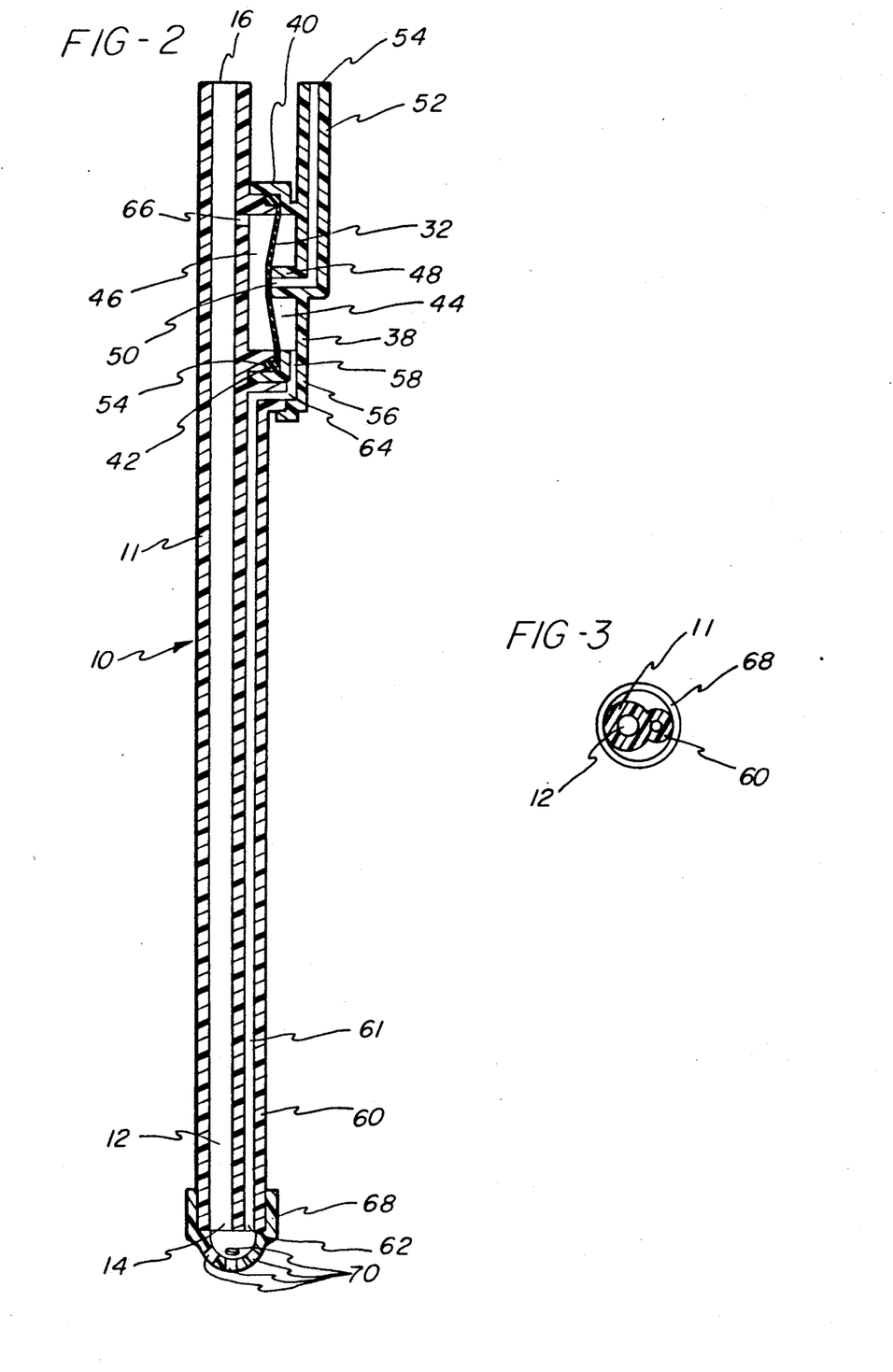
FIG. 2 is a side view of the present invention shown in cross-section.
FIG. 3 is a cross-sectional view taken along line 3—3 in FIG. 1.

Referring to FIGS. 1 and 2, the suction metering and mixing device of the present invention includes an elongated main body 10 including a suction tube 11 having a suction passage 12 formed therethrough. The suction passage 12 includes an inlet opening 14 at a first end of the suction tube 11 to define an inlet for receiving a mixture of blood and anticoagulant into the device and a second end 16 located at an opposite end of the suction tube 11 for connection to a vacuum source via a collection vessel and an air metering valve.

The main body 10 further includes a suction chamber 17 having a base portion 18. The base portion 18 includes a substantially circular base wall 20 which is preferably formed integrally with the suction tube 11 of the main body 10. A substantially circular chamber wall 22 extends from the base portion 20 in a direction away from the tubular main body 10 and defines an inner surface 24 and an outer surface 26 wherein a shoulder portion 28 is formed in the outer surface 26.

A diaphragm 30 having a substantially planar surface 32 and a flange portion 34 extending substantially perpendicularly from the outer edge of the planar surface 32 is positioned such that it extends across the suction chamber 17 with the flange portion 34 being seated on the shoulder portion 28 of the base portion 18. The diaphragm 30 is formed as a flexible element of the chamber 17 and is preferably formed of an elastomeric material.

The chamber 17 further includes a cap portion 36 having a substantially circular top portion 38 and a substantially circular cap wall 40 extending perpendicularly from the top portion 38 and connected to the top portion 38 by means of a shoulder portion 42. The cap 36 is positioned such that the cap wall 40 surrounds the chamber wall 22 and thereby holds the flange portion 34 of the diaphragm 30 in position against the wall 26. In addition, the shoulder portion 42 of the cap 36 engages the outer peripheral portion of the diaphragm 30 to thereby force the flange portion 34 into engagement with the shoulder portion 28 of the base portion 18 whereby the diaphragm 30 is held in position sandwiched between the base portion 18 and the cap 36.

It should be noted that the top portion 38 of the cap 36 is spaced from the shoulder portion 42 whereby a space is defined between the diaphragm surface 32 and the top portion 38 across the diameter of the chamber. Thus, it can be seen that the diaphragm 30 acts to divide the chamber into a first fluid supply portion 44 and a second vacuum portion 46.

The cap 36 is further provided with an inlet tube 48 extending from the top portion 38 a greater distance than the distance between the shoulder portion 42 and the top portion 38 such that an end 50 of the inlet tube 48 contacts the surface 32 of the diaphragm 30 and thereby slightly flexes the diaphragm 30 inwardly toward the base wall 20. The inlet tube 48 is preferably located centrally on the top portion 38 of the cap 36 and the end 50 forms an inlet port for passage of anticoagulant into the first chamber portion 44.

A feed tube 52 is connected to the inlet tube 48 and extends parallel to the suction tube 11. The feed tube 52 includes an inlet end 54 opposite from the inlet tube 48 whereby the feed tube 52 may be connected to a source of anticoagulant to supply anticoagulant to the first chamber portion 44.

The cap 36 is also formed with a tab portion 56 extending in a direction opposite from the feed tube 52. The tab portion 56 includes a supply passage 58 formed integrally therewith defining an outlet port for conveying anticoagulant from the first chamber portion 44. The supply passage 58 is connected to a supply tube 60 extending parallel to and having an interior fluid passage 61 of a lesser diameter than the suction passage 12. The supply tube 60 has a first outlet end 62 located adjacent to the first or inlet end 14 of the suction passage 12 and a second end 64 in fluid communication with the supply passage 58. Thus, the supply tube 60 will convey anticoagulant from the outlet port and supply passage 58 of the first chamber portion 44 to the outlet end 62 where it is in fluid communication with the first end 14 of the suction passage 12.

The second chamber portion 46 acts as a vacuum chamber and includes a fluid connection 66 to the suction passage 12 whereby a vacuum may be supplied to the chamber 46 from the suction passage 12. When a vacuum is supplied to the second chamber portion 46 such that a sub-atmospheric pressure is present within this portion of the chamber, the diaphragm 30 is drawn toward the base wall 20 to open the inlet port 50 and allow anticoagulant to flow into the supply tube 60 via the first chamber portion 44.

As may be seen in FIGS. 2 and 3, the main body portion 10 is formed with a circular cross-section near the outlet 62 of the tube 60 and the inlet 14 of the suction passage 12. A mixing cap 68 in the form of a half-sphere is positioned on the main body 10 over the openings 14, 62 to form a tip portion of the device. The mixing cap 68 includes one or more holes 70 through which blood may enter the device, and the cap 68 forms a mixing chamber for bringing anticoagulant into fluid communication with blood as it is being sucked into the suction passage 12.

Figure 4:
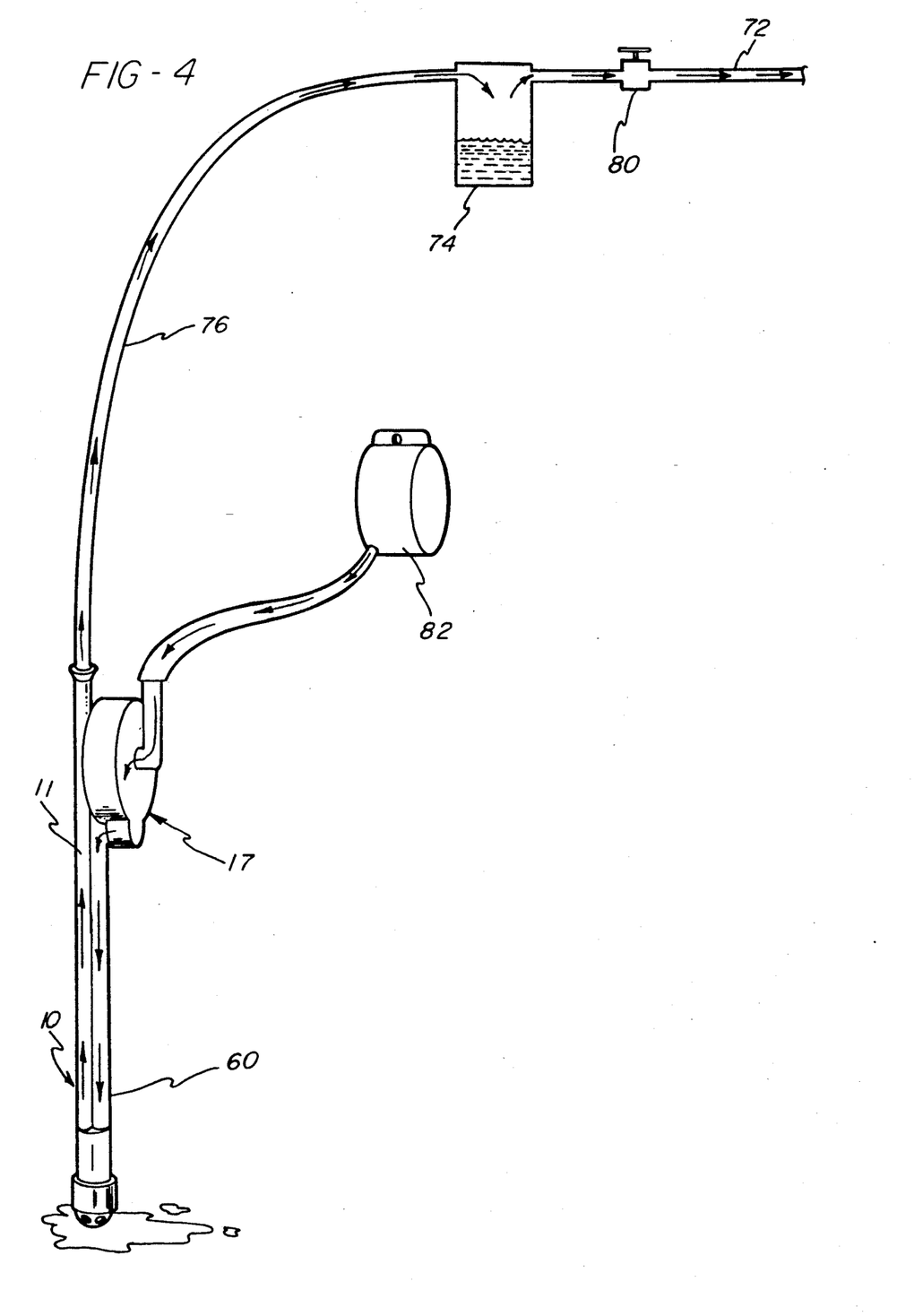
FIG. 4 depicts the suction metering and mixing device of the present invention in combination with a blood collection and processing system.

As may be seen in FIG. 4, the suction metering and mixing device of the present invention may be connected to a suction source which is depicted as including a hospital vacuum line 72 supplying a vacuum to a blood collection and/or processing vessel 74, and a connecting vacuum tube 76 extending from the vessel 74 to the end 16 of the suction tube 11. In addition, an air metering means 80, such as an air metering valve or orifice, is positioned between the hospital vacuum source and the vessel 74. The metering means 80 acts to limit the amount of air drawn through the suction tube 11 when fluid is absent from within the passage 12. Thus, the velocity of air flowing through the suction tube 11 will be limited to a relatively low level such that any pressure drop developed in the second chamber 46 as a result of air flow through the suction tube 11 will not be sufficient to cause the diaphragm 30 to move out of engagement with the inlet port 50, and such that the flow of the first fluid, when present at the inlet port 14, is regulated to a convenient rate.

In operation, the vacuum tube 76 may be connected to the end 16 of the suction tube 11 and a source of anticoagulant 82 may be connected to the inlet end 54 of the drip tube 52 and elevated above the main body 10. The holes 70 in the cap 68 may then be temporarily blocked such that a vacuum will be applied to the second chamber portion 46 to move the diaphragm 30 away from the inlet port 50 and allow anticoagulant to fill the drip feed tube 52, the first chamber 44 and the supply tube 60 whereby the path for supplying anticoagulant is primed for use.

When the holes 70 are unobstructed and no fluid is flowing in the suction passage 12, the second chamber portion 46 will be at near atmospheric pressure such that the diaphragm 30 will be in a rest position in contact with the inlet port 50 whereby flow of anticoagulant into the first chamber portion 44 is prevented. In addition, first chamber portion 44 is prevented. In addition, anticoagulant located within the supply tube 60 is held against flowing out of the tube 60 such that the tube 60 remains in a primed condition.

When a fluid such as blood is aspirated into the device through the holes 70, the pressure within the suction passage 12 decreases such that a vacuum is supplied to the fluid connection 66 to create a sub-atmospheric pressure within the second chamber portion 46, resulting in the diaphragm being repositioned out of contact with the inlet port 50. Consequently, anticoagulant flows into the cavity formed by the mixing cap 68 where it is mixed with blood entering the suction passage 12 and flows with the blood through the suction tube 11 and out of the main body portion 10.

It should be noted that the diameter of the supply tube 60 is selected relative to the diameter of the suction tube 11 such that a precise predetermined amount of anticoagulant will be supplied and mixed with a predetermined volume of blood being aspirated into the passage 12. However, a conventional roller clamp or similar device, at the outlet of the outlet of the source of anticoagulant 82, could be used to reduce the proportion of anticoagulant below this predetermined amount.

Figure 5:
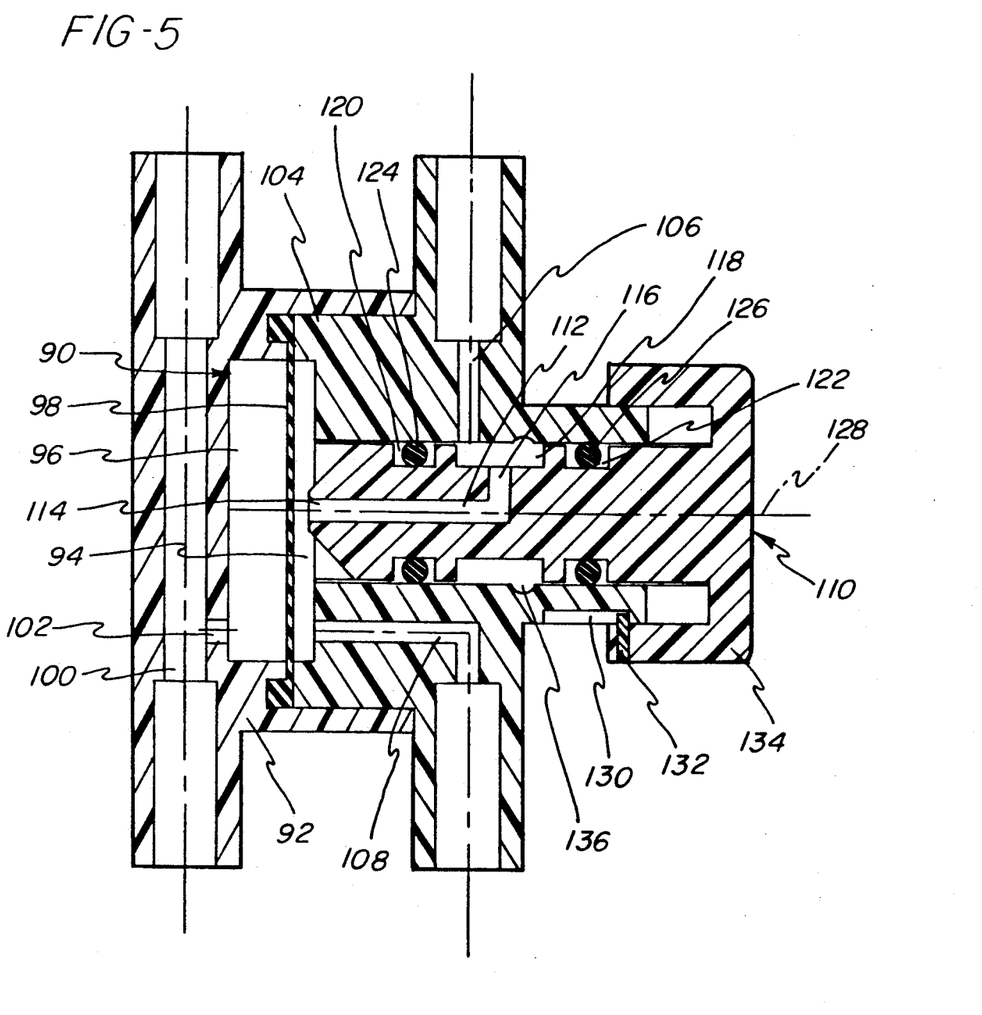
FIG. 5 is a cross-sectional view of an alternative embodiment of the regulator portion of the suction metering and mixing device including an inlet plunger in a non-use position.
Figure 6:
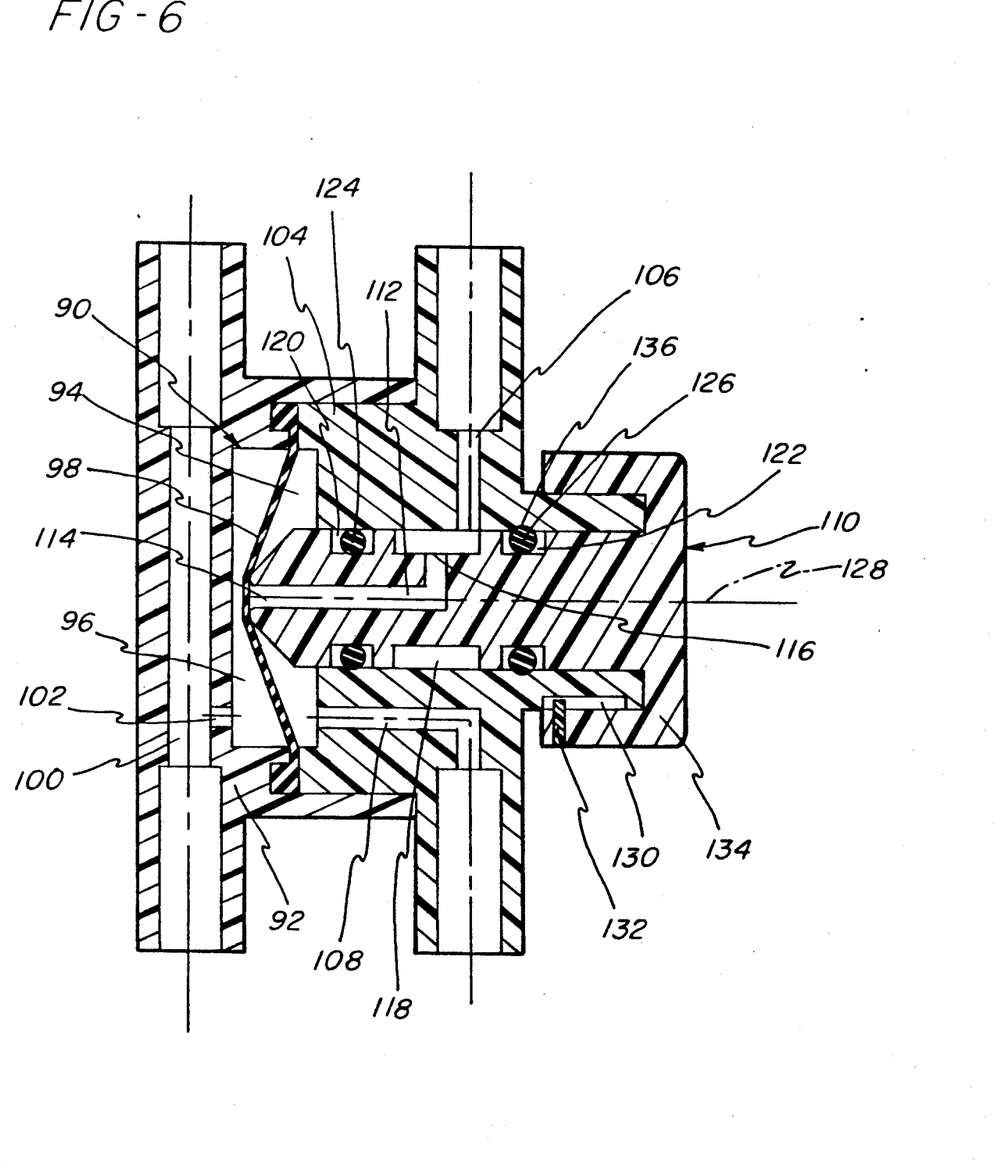
FIG. 6 is a cross-sectional view of the regulator portion of the embodiment of FIG. 5 with the inlet plunger in a position ready for use.
Figure 7:
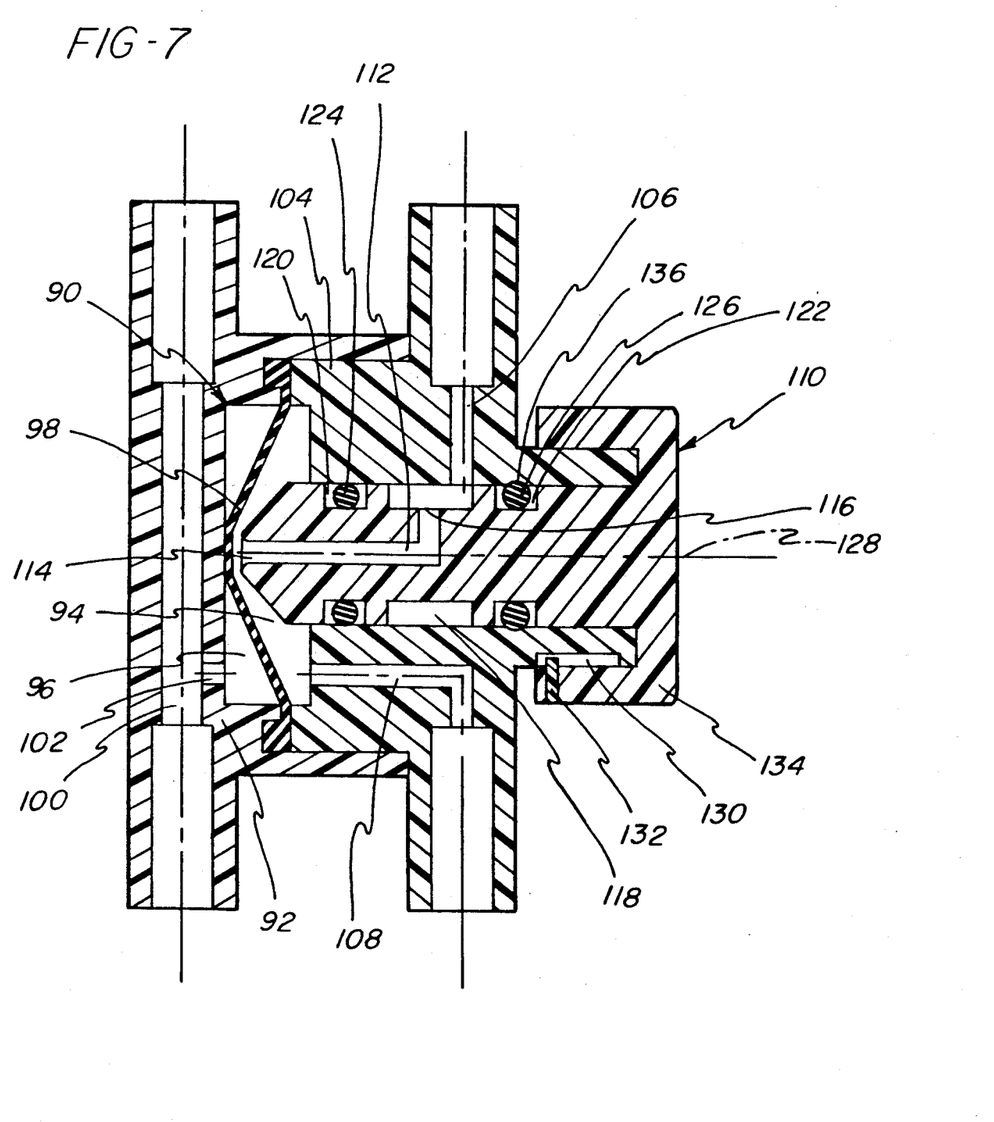
FIG. 7 is a view similar to FIG. 6 in which the diaphragm has been drawn away from the inlet port to permit flow of anticoagulant.

FIGS. 5-7 illustrate a second preferred embodiment of the regulator portion of the suction metering and mixing device including a suction chamber 90 formed in a base portion 92. The suction chamber 90 is divided into first and second portions 94, 96 by means of a flexible diaphragm 98 and the second portion 96 is placed in fluid communication with a suction passage 100 via a connecting passage 102, as in the previous embodiment.

A cap member 104 is provided for holding the diaphragm 98 in place and for defining the first portion 94 of the chamber 90. An inlet port 106 is defined in the cap member 104 and forms a passage for entry of anticoagulant into the chamber. In addition, an outlet passage 108 is defined in the cap member 104 for allowing exit of fluid from the chamber 90.

An elongated substantially cylindrical plunger member 110 extends through a central generally cylindrical aperture in the cap member 104 and defines an intermediate passage 112 for connecting the inlet and outlet ports 106, 108, via chamber 94. The intermediate passage 112 has a first end 114 located in the first chamber portion 94 adjacent to the diaphragm 98. A second end 116 of the intermediate passage 112 opens into a slot 118 formed circumferentially around the plunger 110. In addition, a pair of grooves 120, 122 extend around the plunger member 110 and seal members 124, 126 are located in the grooves 120, 122.

The plunger 110 is mounted for longitudinal movement relative to the base 92 and cap member 104 along an axis 128 of the plunger 110, and the cap member 104 is provided with an elongated slot 130 located on an outer surface thereof for cooperating with a pin 132 affixed to a cap portion 134 of the plunger 110. The slot 130 and pin 132 cooperate to prevent the plunger 110 from being extracted from the cap member 104 and also to limit the rotation of the plunger 110 about its axis 128 relative to the cap member 104.

As seen in FIG. 5, the plunger 110 is located in a storage position with the first end 114 of the intermediate passage 112 out of contact with the diaphragm 98. As the plunger 110 is moved toward the diaphragm 98, the seal member 126 is moved into alignment with a substantially circular groove 136 formed on the interior surface of the cap member. The seal member 126 will then expand slightly such that it is engaged in both groove 122 and groove 136 to resist relative longitudinal movement between the plunger 110 and the cap member 104. This position is illustrated in FIG. 6 in which the diaphragm 98 is shown in a predetermined flexed position in contact with the end of the plunger 110. The plunger 110 may be thus positioned by merely pressing down on the cap 134 of the plunger 110 until the grooves 122 and 136 and the seal member 126 are aligned with each other to prevent outward movement of the plunger 110.

As is depicted in FIG. 7, a suction force applied through the suction passage 100 and connecting passage 102 will draw the diaphragm 98 away from the first end 114 of the intermediate passage 112 whereby fluid may flow from the inlet port 106 into the slot 118, through the intermediate passage 112, into the first chamber portion 94 and out through the outlet port 108. Thus, with the plunger in its use position the present embodiment operates in essentially the same manner as the previous embodiment.

It should be noted that the plunger structure for the regulator portion of the present embodiment of the suction metering and mixing device allows the device to be stored with the diaphragm in an unstressed condition and therefor avoids problems which may occur from the diaphragm resting in a stretched position for an extended period of time prior to use.

It should be noted that the present invention may be formed as a disposable device and the elements of the device, with the exception of the flexible diaphragm and the seals in the second embodiment, are preferably produced from a molded plastic material.

It should be apparent that the present device provides means for accurately initiating and terminating the flow of anticoagulant to be mixed with blood in response to the flow of blood through the suction passage.

While the forms of apparatus herein described constitute preferred embodiments of the invention, it is to be understood that the invention is not limited to these precise forms of apparatus and that changes may be made therein without departing from the scope of the invention which is defined in the appended claims.

What is claimed is:

1. A suction metering and mixing device comprising:
   means defining a suction passage for sucking a first fluid into said device;
   means defining a chamber connected to said means defining said suction passage;
   means defining an inlet port forming a passage for entry of a second fluid into said chamber;
   means defining an outlet port in said chamber forming a passage for allowing said second fluid to exit from said chamber;
   a diaphragm dividing said chamber into first and second portions wherein said inlet and outlet ports are positioned to convey fluid to and from, respectively, said first portion;
   means defining an intermediate passage for connecting said inlet and outlet ports in fluid communication with each other, said intermediate passage being movable toward and away from said diaphragm whereby a first end of said intermediate passage may be positioned into and out of contact with said diaphragm; and
   means for causing said diaphragm to be repositioned from a position in contact with said first end of said intermediate passage to a position spaced from said first end of said intermediate passage.

2. The device of claim 1, wherein said chamber is defined by a base portion and a cap portion, and said means defining said intermediate passage including a plunger extending through said cap portion, said plunger being movable relative to said base and cap portions.

3. The device of claim 2, including a slot formed in a side wall portion of said plunger, said inlet port being located in fluid communication with said slot and said intermediate passage having a second end which opens into said slot.

4. The device of claim 3, wherein said plunger is substantially cylindrical and said slot extends circumferentially around said plunger.

5. The device of claim 3, wherein said plunger is substantially cylindrical and includes means for cooperating with said cap portion for limiting relative rotation between said plunger and said cap portion.

6. The device of claim 2, wherein said plunger includes a groove extending around the circumference of said plunger and a seal member is positioned in said groove for movement with said plunger.

7. The device of claim 6, including a groove formed in said cap portion adjacent to said plunger, wherein said seal member simultaneously engages said grooves in said plunger and said cap portion to retain said plunger in a predetermined position with said first end of said intermediate passage in engagement with said diaphragm.

8. The device of claim 7, including a slot formed in said plunger intermediate said diaphragm and said groove in said plunger, said inlet port being located in fluid communication with said slot and said intermediate passage having a second end which opens into said slot.

9. The device of claim 8, including a second groove and a second seal member located in said second groove intermediate said slot and said diaphragm.

10. The device of claim 1, wherein said means for causing said diaphragm to be repositioned includes means defining a passage placing said second chamber portion in fluid communication with said suction passage.

11. The device of claim 1, wherein said diaphragm is formed of a flexible material and said movement of said first end of said intermediate passage toward said diaphragm causes said diaphragm to be flexed toward said suction passage.

12. A suction metering and mixing device comprising:
   means defining a suction passage for sucking a first fluid into said device;
   means defining a chamber connected to said means defining said suction passage;
   means defining an inlet port forming a passage for entry of a second fluid into said chamber;
   means defining an outlet port in said chamber forming a passage for allowing said second fluid to exit from said chamber;
   a flexible diaphragm dividing said chamber into first and second portions wherein said inlet and outlet ports are positioned to convey fluid to and from said first portion, respectively;
   a plunger including means defining an intermediate passage for connecting said inlet and outlet ports in fluid communication with each other, said plunger being movable toward and away from said diaphragm whereby a first end of said intermediate passage may be positioned into and out of contact with said diaphragm; and means defining a passage between said second chamber portion and said suction passage whereby a vacuum within said suction passage causes said diaphragm to be repositioned from a position in contact with said first end of said intermediate passage to a position spaced from said first end of said intermediate passage.

13. The device of claim 12, wherein said plunger is formed as an elongated member movable along a longitudinal axis thereof to position said first end of said intermediate passage in contact with said diaphragm.

14. The device of claim 12, wherein said chamber is defined by a base portion and a cap portion, said cap portion including means defining a groove, said plunger including means defining a groove and having a seal member positioned therein, said seal member cooperating with said groove in said cap portion when said first end of said intermediate passage is positioned in contact with said diaphragm.

15. The device of claim 14, wherein said plunger includes a slot and said intermediate passage includes a second end which opens into said slot, said inlet port being located in fluid communication with said slot and said second intermediate passage end.

* * * * *